US00PP36938P2

(12) United States Plant Patent
de Wagt

(10) Patent No.: US PP36,938 P2
(45) Date of Patent: Sep. 2, 2025

(54) ***HELIOPSIS* PLANT NAMED 'VENSGC'**

(50) Latin Name: *Heliopsis helianthoides*
Varietal Denomination: VENSGC

(71) Applicant: Marcel de Wagt, Ven-Zelderheide (NL)

(72) Inventor: Marcel de Wagt, Ven-Zelderheide (NL)

( * ) Notice: Subject to any disclaimer, the term of this patent is extended or adjusted under 35 U.S.C. 154(b) by 0 days.

(21) Appl. No.: 18/938,360

(22) Filed: Nov. 6, 2024

(30) Foreign Application Priority Data

Apr. 11, 2024 (QZ) ..... PBR 2024/0851

(51) Int. Cl.
*A01H 5/02* (2018.01)
*A01H 6/14* (2018.01)

(52) U.S. Cl.
USPC ..... Plt./437

(58) Field of Classification Search
USPC ..... Plt./263.1, 437
See application file for complete search history.

(56) References Cited

PUBLICATIONS

Plantipp, Peter. Jul. 11, 2024 Facebook post. https://www.facebook.com/story.php/?story_fbid=1041894801097021&id=100058295330890&_rdr. 1 page (Year: 2024).*

Concept Plants website. *Heliopsis* Orange Martble ('VENSGC'). https://conceptplants.com/varieties/heliopsis-orange-marble-vensgc. 1 page. (Year: 2024).*

* cited by examiner

*Primary Examiner* — Karen M Redden
(74) *Attorney, Agent, or Firm* — Cassandra Bright

(57) ABSTRACT

A new and distinct cultivar of *Heliopsis* plant named 'VENSGC' is disclosed, characterized by unique green, red, and yellow-marbled foliage, and warm orange flowers with yellow-orange tips. The flowering period is long, from July until late September. Plants are useful for outdoor ornamental purposes, normally produced as an outdoor garden or container plant.

2 Drawing Sheets

Latin name of the genus and species: *Heliopsis helianthoides.*
Variety denomination: 'VENSGC'.

BACKGROUND OF THE INVENTION

The new cultivar *Heliopsis* 'VENSGC' was discovered by the inventor as a chance seedling growing in a container at a nursery in Ven-Zelderheide, the Netherlands in 2018. The parents are unknown.

'VENSGC' was first asexually reproduced by vegetative cuttings at a nursey in Haarlem, the Netherlands in 2019, and has been found to retain its distinctive characteristics through successive asexual propagations.

SUMMARY OF THE INVENTION

The following are the most outstanding and distinguishing characteristics of the new cultivar when grown under normal horticultural practices:

1. Unique marbled foliage.
2. Chocolate-brown flower buds open to orange flowers with bright yellow-orange tips.
3. Long flowering period (July until late September).

COMPARISON WITH PARENT VARIETIES

The seed and pollen parents are unknown.

COMPARISON WITH COMMERCIAL CULTIVARS

'VENSGC' can be compared to the commercial variety *Heliopsis* 'Fire Twister', U.S. Plant Pat. No. 33,733. Plants of the two varieties are similar in most horticultural characteristics, however, 'VENSGC' differs in the following:

1. Foliage color of the new variety is marbled green, yellow and red, while the foliage color of this comparator is solid dark green.
2. Flower color of the new variety is warm orange, while the flower color of this comparator is more red-orange.

'VENSGC' can be compared to the commercial variety *Heliopsis* 'Funky Spinner', U.S. Plant Pat. No. 33,715. Plants of the two varieties are similar in most horticultural characteristics, however, 'VENSGC' differs in the following:

1. Foliage color of the new variety is marbled green, yellow and red, while the foliage color of this comparator is solid dark green.
2. Flower color of the new variety is warm orange, while the flower color of this comparator is yellow with an orange center.

'VENSGC' can be compared to the commercial variety *Heliopsis* 'Bleeding Heart', unpatented. Plants of the two varieties are similar in most horticultural characteristics, however, 'VENSGC' differs in the following:

1. Foliage color of the new variety is marbled green, yellow and red, while the foliage color of this comparator is solid dark green.
2. Flower color of the new variety is warm orange, while the flower color of this comparator is more reddish-orange.

'VENSGC' can be compared to the commercial variety *Heliopsis* 'Sunburst', unpatented. Plants of the two varieties are similar in most horticultural characteristics, however, 'VENSGC' differs in the following:

1. Foliage color of the new variety is marbled green, yellow and red, while the foliage color of this comparator is variegated white and green.
2. Flower color of the new variety is warm orange, while the flower color of this comparator is light orange-yellow.

'VENSGC' can be compared to the commercial variety *Heliopsis* 'Loraine Sunshine', U.S. Plant Pat. No. 10,690. Plants of the two varieties are similar in most horticultural characteristics, however, 'VENSGC' differs in the following:

1. Foliage color of the new variety is marbled green, yellow and red, while the foliage color of this comparator is variegated white and green.
2. Flower color of the new variety is warm orange, while the flower color of this comparator is light orange-yellow.

'VENSGC' can be compared to the commercial variety *Heliopsis* 'Summer Pink', U.S. Plant Pat. No. 23,390. Plants of the two varieties are similar in most horticultural characteristics, however, 'VENSGC' differs in the following:

1. Foliage color of the new variety is marbled green, yellow and red, while the foliage color of this comparator is variegated pink, white and green.
2. Flower color of the new variety is warm orange, while the flower color of this comparator is light yellow.

BRIEF DESCRIPTION OF THE PHOTOGRAPHS

The present invention of a new and distinct variety of *Heliopsis* is shown in the accompanying photographs, the colors being as nearly true as possible with color photographs of this type.

DETAILED BOTANICAL DESCRIPTION

Figure 1:
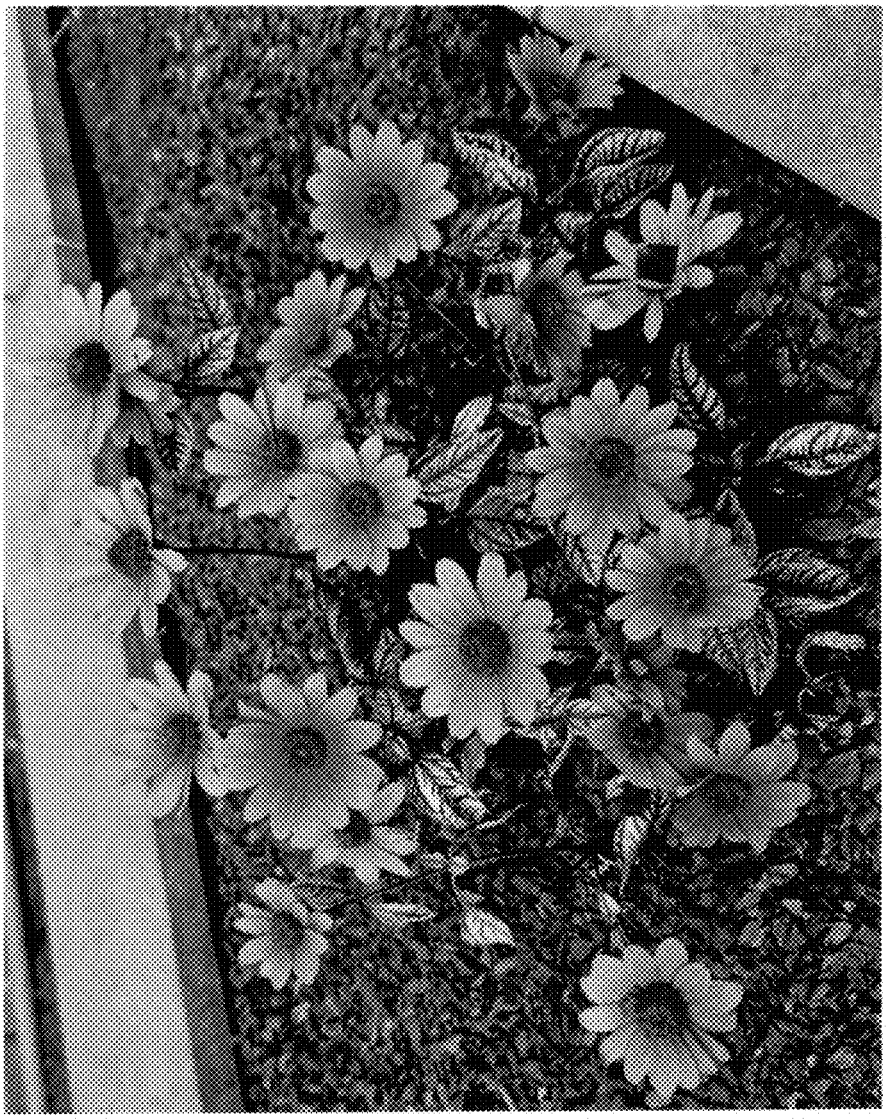
FIG. 1 illustrates a plant of approximately 6 months planted in the ground.
Figure 2:
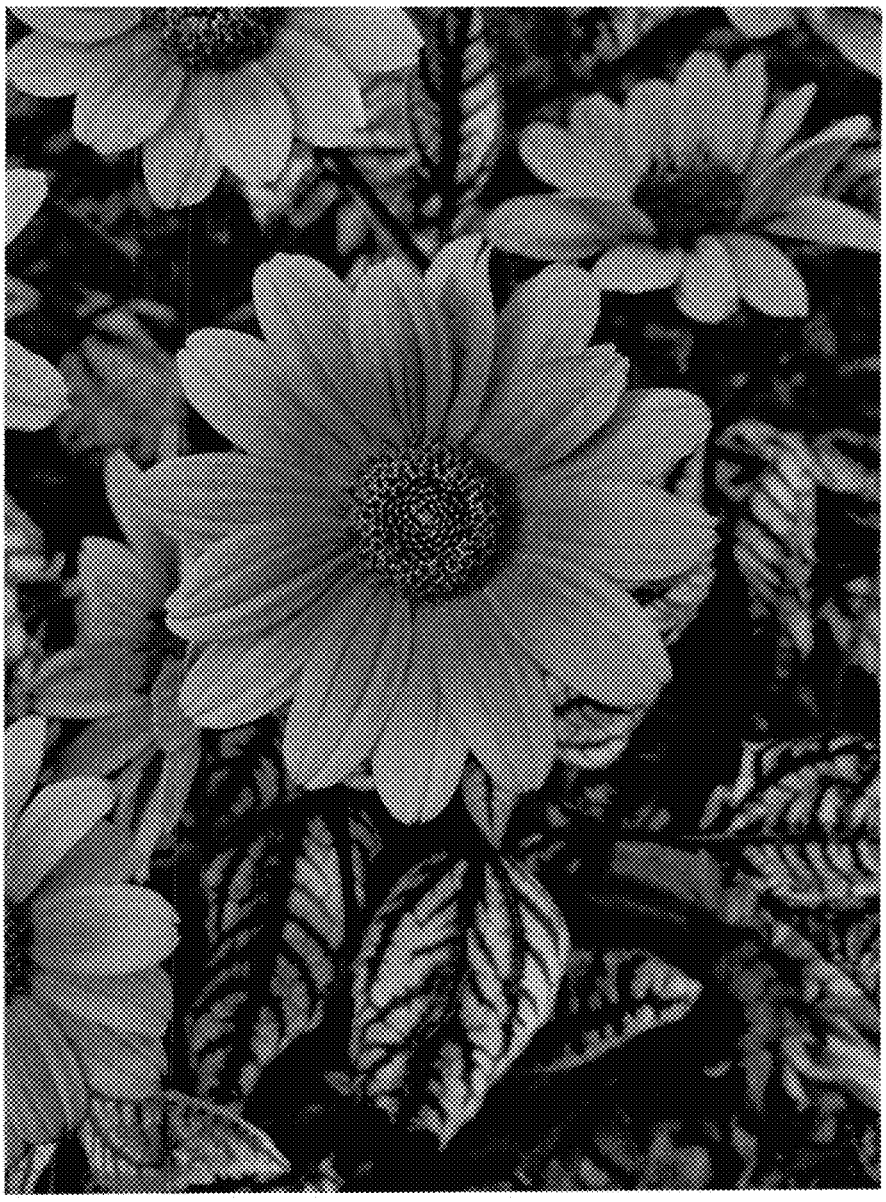
FIG. 2 illustrates a close up of the inflorescence and foliage.

In the following description, color references are made to The Royal Horticultural Society Color Chart, 2015 edition, except where general terms of ordinary dictionary significance are used. The following observations and measurements describe 'VENSGC' plants grown outdoors in Ven-Zelderheide, the Netherlands. Temperatures ranged from about 2° C. to 32° C. No artificial light, photoperiodic treatments or chemical treatments were given to the plants. Measurements and numerical values represent averages of typical plant types.

Botanical classification: *Heliopsis helianthoides* 'VENSGC'.

PROPAGATION

Typical method: Tissue culture.

Time to initiate roots: From stage 3 to stage 4: 6 to 7 weeks.

From rooted plug to P9: 10 to 12 weeks.

PLANT

Plant type: Herbaceous perennial.

Growth habit: Dwarf, spreading-upright.

Height: 45 cm.

Plant spread: 60 cm.

Growth rate: Moderate.

Branches:

*Shape*.—Rounded.

*Strength*.—Moderately strong to strong.

*Length*.—Average 42 cm.

*Diameter*.—Average 6 mm.

*Habit*.—Freely branching.

*Texture*.—Slightly pubescent.

*Color*.—RHS Greyed-Purple 187A with some Yellow-Green 144B.

Root description: Fibrous, Brown N199A.

FOLIAGE

*Arrangement*.—Simple, opposite.

*Length*.—4 cm.

*Width*.—2 cm.

*Shape*.—Ovate.

*Apex*.—Acute.

*Base*.—Obtuse, nearly truncate.

*Margin*.—Serrate.

*Texture of top surface*.—Rugose, slightly pubescent.

*Texture of bottom surface*.—Rugose, slightly pubescent.

*Color*.—Young foliage upper side: RHS Yellow-Green N189A, Red-Purple 60A at margins. Young foliage under side: RHS Green NN137B to NN137C, with occasional blotches of Yellow-Green 147C. Red-Purple 60A at margins. Mature foliage upper side: RHS Green NN137A with Yellow 1C, Red-Purple 60A and Yellow-Green 150C. Mature foliage under side: RHS Green NN137C with Red-Purple 60A and Green-Yellow 1C.

*Venation*.—Type: Pinnate. Color, young, upper side: Mid vein RHS Red-Purple 60A. Smaller veins faded Red-Purple 60A. Color, young, under side: Mid vein RHS Greyed-Purple 187B, smaller veins faded Greyed-Purple 187B. Color, mature, upper side: Mid vein RHS Greyed-Purple 187B. Color, mature, under side: RHS Greyed-Purple 187B.

Petiole:

*Length*.—1.5 cm.

*Diameter*.—2 mm.

*Texture*.—Slightly pubescent.

*Strength*.—Strong.

*Color*.—Upper side: RHS Greyed-Green N189A. Under side: RHS Greyed-Purple 187B.

FLOWER

Bloom period: July to late September in the Netherland.

Inflorescence:

*Type/form*.—Rotate, terminal capitulum consisting of a receptacle, disc florets and ray florets.

Quantity.—Average 23 per plant at one time.

*Diameter*.—6 cm.

*Depth*.—2.5 cm.

Fragrance: None.

Bud:

*Shape*.—Cup-shaped.

*Length*.—1.2 cm.

*Diameter*.—2.5 cm.

*Texture*.—Matte, moderately covered with hairs.

*Color*.—RHS Yellow-Green 144B with hint of Greyed-Purple 187A.

Ray florets:
*Quantity*.—Average 18.
*Shape*.—Oblong, elongated, with 2 ribs running vertically.
*Arrangement*.—Rotate.
*Length*.—2 cm.
*Width*.—1.4 cm.
*Apex*.—Rounded with 3 shallow indentations.
*Base*.—Attenuate.
*Margin*.—Entire.
*Texture*.—Smooth.
*Color*.—Upper surface at first opening: RHS Greyed-Orange N163B base Orange-Red N34A. Under surface at first opening: RHS Greyed-Orange N163B base Orange-Red N34A. Upper surface at maturity: RHS Yellow 17A base Orange-Red 34B. Under surface at maturity: RHS Greyed-Orange 163A and 163B with hint of N163C. Stripes Greyed-Purple 184B.

Disc florets:
*Quantity*.—Approximately 100 to 120.
*Length*.—Approximately 7 mm.
*Width*.—Approximately 2 mm.
*Shape*.—Tubular.
*Apex*.—Acute.
*Margin*.—Entire.
*Texture*.—Glabrous.
*Color*.—Immature: Greyed-Orange 171B with Greyed-Red 181A. Mature: Greyed-Purple 183C. Occasional hint of Violet 90A. Tube is White 155A at base, Yellow-Green 144D at center.

Involucral bracts:
*Arrangement*.—Rotate, fused.
*Number*.—Average 20.
*Depth*.—1 cm, including receptacle.
*Width*.—3 cm.
*Shape*.—Oblong.
*Texture*.—Glossy, moderately pubescent.
*Apex*.—Acute.
*Base*.—Broadly cuneate.
*Margin*.—Entire.
*Color*.—RHS Yellow-Green 144A to 144C, with Greyed-Purple 187A.

Peduncle:
*Length*.—17 cm.
*Diameter*.—4 mm.
*Color*.—RHS Greyed-Purple 187A.
*Texture*.—Moderately covered in short hairs.

Receptacle:
*Width*.—2 cm.
*Depth*.—1 cm.
*Color*.—RHS Yellow-Green 144A to 144C with Greyed-Purple 187A.

REPRODUCTIVE ORGANS

Ray florets:
Gynoecium:
*Pistil number*.—1.
*Pistil length*.—4 mm.
*Pistil width*.—Less than 1 mm.
*Style length*.—3 mm.
*Style color*.—RHS Orange-Red 31B.
*Stigma shape*.—Bifid.
*Stigma color*.—RHS Red-Purple 59A.
*Ovary length*.—3 mm.
*Ovary width*.—2 mm.
*Ovary color*.—RHS Yellow-Green 144C.
Androecium: Not present.

Disc florets:
Gynoecium:
*Pistil number*.—1.
*Pistil length*.—3 mm.
*Pistil width*.—Less than 1 mm.
*Style length*.—2 mm.
*Style color*.—Near RHS Greyed-Orange 171A.
*Stigma shape*.—Bifid.
*Stigma color*.—RHS Greyed-Purple 183C.
Androecium:
*Stamens number*.—5.
*Stamens length*.—3 mm.
*Stamens width*.—1 mm.
*Anther shape*.—Linear.
*Anther length*.—3 mm.
*Anther width*.—1 mm.
*Anther color*.—RHS Brown 200A.
*Pollen quantity*.—Moderate.
*Pollen color*.—RHS Yellow 12A.

OTHER CHARACTERISTICS

Disease and pest resistance: Neither resistance nor susceptibility to additional normal diseases and pests of *Heliopsis* has been observed.

Fruit/seed production: Not observed.

What is claimed is:

1. A new and distinct cultivar of *Heliopsis* plant named 'VENSGC' as described and shown herein.

* * * * *